(12) United States Patent
Klee et al.

(10) Patent No.: US 12,151,005 B2
(45) Date of Patent: Nov. 26, 2024

(54) DENTAL COMPOSITION

(71) Applicants: DENTSPLY SIRONA Inc., York, PA (US); DENTSPLY DETREY GMBH, Constance (DE)

(72) Inventors: Joachim E. Klee, Radolfzell (DE); Matthias Worm, Singen (DE); Christian Scheufler, Engen (DE); Oliver Elsner, Radolfzell (DE); Thomas Tigges, Constance (DE)

(73) Assignee: DENTSPLY SIRONA INC., York, PA (US)

( * ) Notice: Subject to any disclaimer, the term of this patent is extended or adjusted under 35 U.S.C. 154(b) by 746 days.

(21) Appl. No.: 17/414,528

(22) PCT Filed: Dec. 17, 2019

(86) PCT No.: PCT/EP2019/085794
§ 371 (c)(1),
(2) Date: Jun. 16, 2021

(87) PCT Pub. No.: WO2020/127380
PCT Pub. Date: Jun. 25, 2020

(65) Prior Publication Data
US 2022/0062117 A1   Mar. 3, 2022

(30) Foreign Application Priority Data
Dec. 19, 2018 (EP) ..................... 18214198

(51) Int. Cl.
*A61K 6/893* (2020.01)
*A61K 6/30* (2020.01)
*A61K 6/62* (2020.01)
*A61K 6/889* (2020.01)
*C08L 35/02* (2006.01)

(52) U.S. Cl.
CPC ............ *A61K 6/893* (2020.01); *A61K 6/30* (2020.01); *A61K 6/62* (2020.01); *A61K 6/889* (2020.01); *C08L 35/02* (2013.01)

(58) Field of Classification Search
CPC .................. A61K 6/887; A61K 6/893
See application file for complete search history.

(56) References Cited

PUBLICATIONS

Szafran, M.; Rokicki, G.; Czerwińska, L.; Bobryk, E. Kompozyty 2008, 1, 47-52. (Year: 2008).*

* cited by examiner

*Primary Examiner* — Michael F Pepitone
(74) *Attorney, Agent, or Firm* — DENTSPLY SIRONA INC.

(57) ABSTRACT

Described herein is a dental composition containing a polymerizable compound having at least one optionally derivatized β-hydroxy urethane unit. The polymerizable compound having at least one optionally derivatized β-hydroxy urethane unit is obtained without use of organo-metal catalysts and isocyanates and by a reaction between an at least one component A having at least one cyclic carbonate group with an at least one component B having at least one of primary amine functional group and secondary amine functional group. The present disclosure relates to use of the polymerizable compound having at least one optionally derivatized β-hydroxy urethane unit for the preparation of a dental composition, in particular a dental composite, a glass ionomer, a dental cement, a dental sealant, and a dental adhesive.

3 Claims, 1 Drawing Sheet

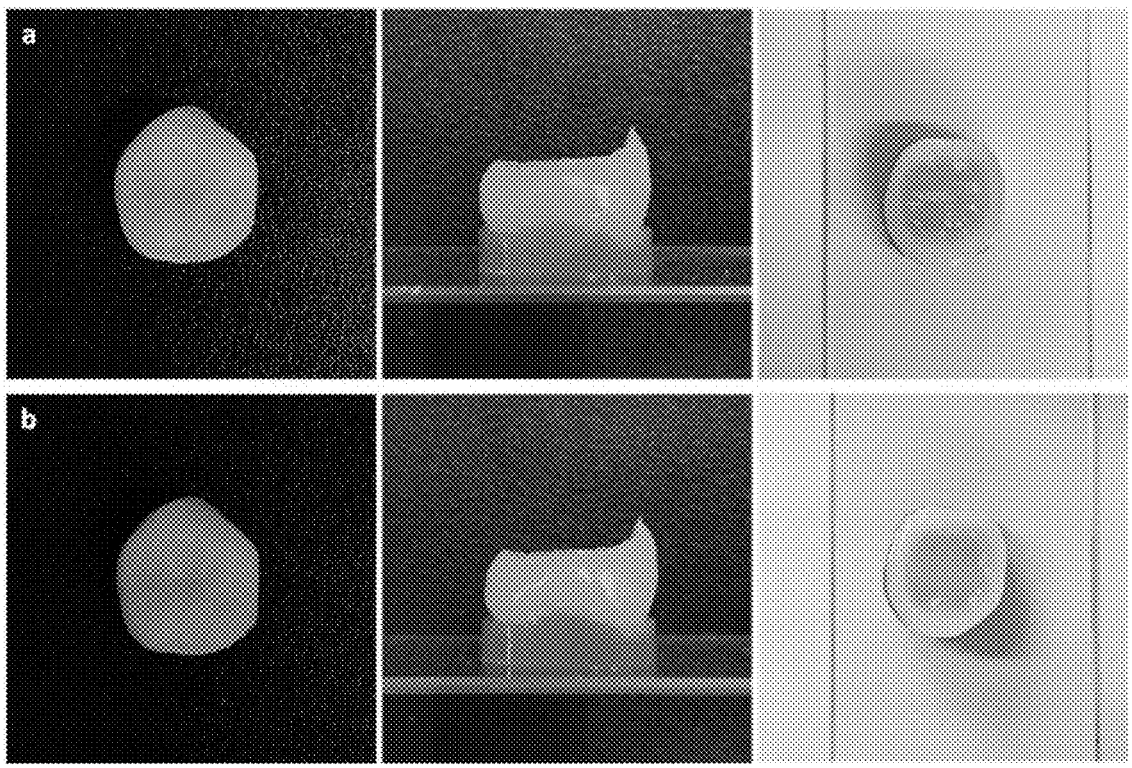

DENTAL COMPOSITION

FIELD OF THE INVENTION

The present disclosure relates to a dental composition containing a polymerizable compound having at least one optionally derivatized β-hydroxy urethane unit. The polymerizable compound having at least one optionally derivatized β-hydroxy urethane unit is obtained without use of organometal catalysts and isocyanates and by a reaction between an at least one component A having at least one cyclic carbonate group with an at least one component B having at least one of primary amine functional group and secondary amine functional group. The present disclosure relates to use of the polymerizable compound having at least one optionally derivatized β-hydroxy urethane unit for the preparation of a dental composition, in particular, a dental composite, a glass ionomer, a dental cement, a dental sealant, and a dental adhesive.

BACKGROUND OF THE INVENTION

Currently, various urethane methacrylates are synthesized by reaction of hydroxyalkyl methacrylates with diisocyanates catalyzed by organo-stannyl compounds. Diisocyanates are known as toxic substances and its use pose various health risk to humans and the environment. Also, due to the toxicity of the stannyl compounds, for example, Dibutyl tin laurate, an alternative with a less toxic metal compound or a metal free synthesis is desired.

Carbonate-amine reaction serves as an alternative for the formation of β-hydroxy urethane methacrylates without the use of isocyanates.

U.S. Pat. No. 5,977,262 discloses a process for the preparation of hydroxyurethanes comprising: contacting a cyclic carbonate, a primary amine, and a catalytically effective amount of a base whose conjugate acid has a pKa of about 11 or more.

The reaction from a diamine and a molecule having at least two cyclic carbonate functional groups results in the formation of polyhydroxyurethane.

U.S. Pat. No. 8,118,968 discloses a bonding agent system that contains at least components (A) and (B), where (A) is at least one compound with at least two cyclic carbonate groups and (B) is at least one compound with at least two primary and/or secondary amine groups. The reaction between component (A) and component (B) takes place in the presence of a catalytic amount of bases. The bonding agent system is particularly suitable for use as a two-component adhesive or sealant and has very good adhesion to various substrates.

U.S Pat. Appl. No 2016/0122473 relates to monofunctional or multifunctional acrylated or methacrylated urethane oligomer where said urethane bond is obtained without use of isocyanate and by the carbonate-amine reaction between a cyclic carbonate and a monoamine or polyamine, with subsequently the conversion of the hydroxyls in the β-position with respect to the urethane bond into ester-acids by reaction with a cyclic anhydride, which reaction is followed by the conversion of said acid functional groups into acrylated or methacrylated end groups by reaction with a polyepoxide compound in the presence of acrylic or methacrylic acid. Said oligomer is used as crosslinkable binder for a functionality of at least 2 in coating, molding, leak tightness agent or sealing compositions or, if monofunctional, as macromonomer in polymerizable compositions for the production of grafted polymers. The carbonate-amine reaction between a cyclic carbonate and a monoamine or polyamine is carried in presence of tri-phenylphosphite.

U.S Pat. Appl. No 2017/0342024 describes an acrylated and/or methacrylated urethane oligomer obtained by reaction of a specific polyamine a) with a cyclic carbonate compound b) carrying m cyclic carbonate groups, giving an intermediate product c) carrying m formed urethane groups which carry residual reactive amine —NH— groups, and subsequently an addition reaction of each of the said residual reactive amine groups of the said product c) with an acrylate group of a compound d) carrying, in addition to the said acrylate group, p additional acrylate and/or methacrylate groups, with each residual reactive amine —NH— group of the said product c) being thus converted into a carbon-nitrogen bond carrying the said acrylate and/or methacrylate groups, and thus production of the said urethane oligomer, with each carbon-nitrogen bond formed carrying p acrylate and/or methacrylate groups and the said urethane oligomer carrying m urethane groups and m hydroxyl groups in the alpha or beta position with respect to the said urethane and having a functionality in acrylates and/or methacrylates ranging from m*p(n−1) to m*p(2n−2). The invention also relates to a process for the preparation of the said oligomer in two stages, to the intermediate product c) and to the use of the said urethane oligomer in crosslinkable compositions, in particular in coating compositions, adhesive compositions, compositions for systems for the layer-by-layer manufacture of 3D objects, compositions for 3D printing systems, moulding compositions, leak tightness agent compositions, chemical sealing compositions, concrete compositions or composite compositions. The carbonate-amine reaction between a cyclic carbonate and a monoamine or polyamine is carried out in presence of tris(nonylphenyl)phosphite and 2,6-di(tert-butyl)-4-methylphenol(BHT).

U.S Pat. Appl. No 2018/0120700 describes a photosensitive resin composition, comprising: (a) photo-polymerizable unsaturated compound, (b) hydroxyurethane compound, and (c) photoinitiator. The photosensitive resin composition can be used as photoresist coating for dry film photoresist to manufacture the electronic components, such as print circuit board and so on. Further, the (b) hydroxyurethane compound having [CC]/[NH$_2$] between 0.5 and 0.9, which increases the resolution, adhesion, and strip-ping ability of photosensitive resin composition for dry film photoresist, and improves the effectiveness and the quality of dry film photoresist for manufacturing printed circuit board and other electric component. The carbonate-amine reaction between a cyclic carbonate and a polyamine is carried out at 160° C.

Japanese Patent Publication No. 2008-239881 discloses a radiation-curable resin composition, as well as method for manufacturing cured material using the same and photo semiconductor.

OBJECTIVE OF THE PRESENT INVENTION

It is an object of the present disclosure to provide dental compositions, in particular dental composites, which are useful as filling materials, light curable cements and glass ionomers, pit and fissure sealants to prevent caries, as an adhesive between tooth structure and/or bone and polymeric composites, whereby the dental composition has excellent storage stability and long-term mechanical resistance.

SUMMARY OF THE INVENTION

In a first aspect of the present disclosure, a dental composition is provided comprising:
(a) a polymerizable compound having at least one optionally derivatized β-hydroxy urethane unit obtained by a process comprising the steps of:
(i) reacting an at least one component A having at least one cyclic carbonate group with an at least one component B having at least one of primary amine functional group and secondary amine functional group to form the polymerizable compound having at least one β-hydroxy urethane unit or an intermediate compound having at least one β-hydroxy urethane unit and the residual —NH or —OH group;
(ii) optionally reacting the intermediate compound having at least one β-hydroxy urethane unit and the residual —NH or —OH group with an at least one unsaturated mono- or poly-carboxylic acid to form the polymerizable compound having at least one optionally derivatized β-hydroxy urethane unit; and
(b) at least one of filler and solvent;
wherein the polymerizable compound having at least one optionally derivatized β-hydroxy urethane unit is one of Formula IIIa-IIIg:

Formula IIIa
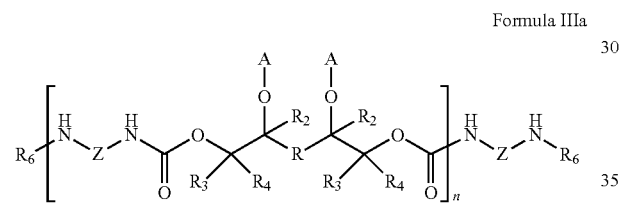

Formula IIIb
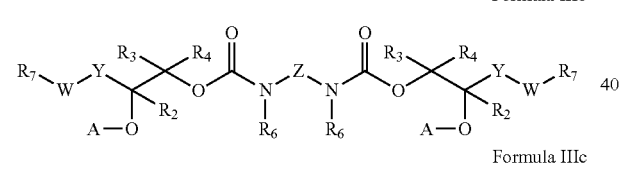

Formula IIIc
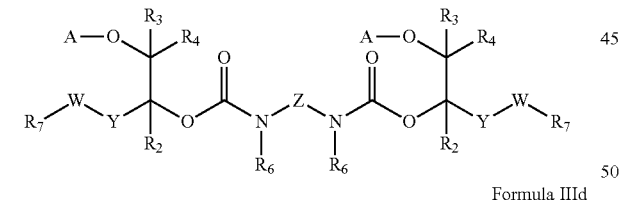

Formula IIId
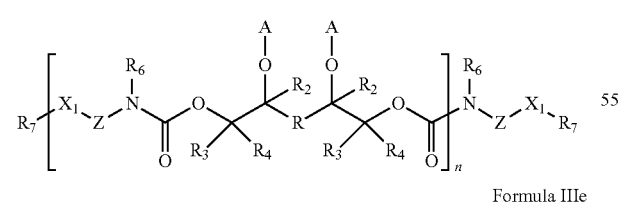

Formula IIIe
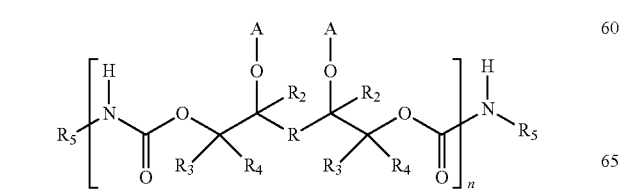

Formula IIIf
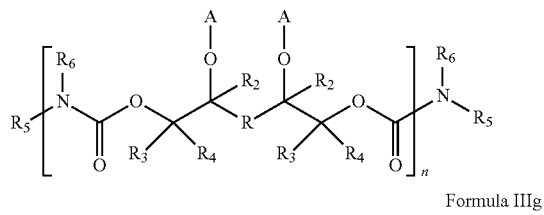

Formula IIIg
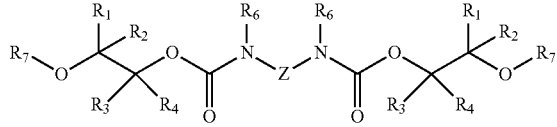

wherein
R represents a divalent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or unsubstituted or substituted $C_3$-$C_{18}$ heteroarylene group;

$R_1$ is an unsubstituted or substituted $C_{2-10}$ alkyl group, an unsubstituted or substituted $C_3$-$C_6$ cycloalkyl group, an unsubstituted or substituted $C_1$-$C_8$ cycloalkylalkylene, an unsubstituted or substituted $C_5$-$C_{18}$ aryl group, an unsubstituted or substituted $C_7$-$C_{24}$ aralkyl group, wherein each substituted group is substituted by one or more of a $C_{1-4}$ alkyl group, a $C_{1-4}$ alkoxy group, a hydroxyl group, an aryl group or an aryloxy group;

$R_2$, $R_3$ and $R_4$ are independent from each other, and represent a hydrogen or a $C_{1-4}$ alkyl group;

Z is a divalent aliphatic $C_{2-10}$ group, a divalent cycloaliphatic $C_3$-$C_6$ group or an aralkylene group having 7 to 24 carbon atoms, wherein each group optionally contain oxygen atoms and which is optionally substituted by $C_{1-4}$ alkyl group;

$R_5$ is a mono-valent aliphatic $C_{1-10}$ group, cycloaliphatic $C_3$-$C_6$ group or an aralkylene group having 7 to 24 carbon atoms;

$R_6$ is a hydrogen atom, a $C_{1-6}$ alkyl group, a $C_{3-10}$ cycloalkyl group, a $C_7$-$C_{12}$ aralkyl group, or an (meth) acryl group; wherein each group is optionally substituted by one or more of a $C_{1-4}$ alkyl group, a $C_{1-4}$ alkoxy group, or a hydroxyl group;

$R_7$ is

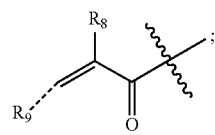

wherein $R_8$ is a hydrogen atom, or a linear $C_{1-3}$ or branched $C_{3-5}$ alkyl group substituted with a COOH group;

$R_9$ is a hydrogen atom, —COOH group, or a linear $C_{1-3}$ or branched $C_{3-5}$ alkyl group substituted with a COOH group;

A is independently same or different and is a hydrogen atom or $R_7$;

W is an oxygen atom; Y is $C_1$-$C_4$ alkylene; $X_1$ is an oxygen atom or a nitrogen atom substituted by $R_6$; and n is an integer of from 1 to 5.

BRIEF DESCRIPTION OF THE FIGURES

Objects, features, and advantages of the present invention will also become apparent upon reading the following description in conjunction with the figures, in which:

FIG. 1a exhibits the use of a dental composition in accordance with embodiments of the present invention for a 3D-printing process for manufacturing dental objects, such as dental crown.

FIG. 1b exhibits the use of a dental composition in accordance with comparative embodiments outside of the present invention for a 3D-printing process for manufacturing dental objects, such as dental crown.

DETAILED DESCRIPTION OF THE INVENTION

Some of the terms used in the present disclosure are defined below:

The term "alkyl", unless otherwise specified, refers to a monoradical branched or unbranched saturated hydrocarbon chain having from 1 to 18 carbon atoms. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, dodecyl, tetradecyl, and the like. Alkyl groups may be substituted further with one or more substituents selected from alkenyl, alkoxy, and hydroxyl.

The term "alkylene", unless otherwise specified refers to a linear saturated divalent hydrocarbon radical of one to eighteen carbon atoms or a branched saturated divalent hydrocarbon radical of three to eighteen carbon atoms, e.g., methylene, ethylene, 2,2-dimethylethylene, propylene, 2-methylpropylene, butylene and the like, preferably methylene, ethylene, or propylene.

The term "alkoxy" is a functional group containing an alkyl group bonded to an oxygen atom. The $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

The term "arylene" is the divalent moiety of "aryl". The term "aryl" refers to C5-C18-membered aromatic, heterocyclic, fused aromatic, fused heterocyclic, biaromatic, or biheterocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those "aryl" groups having heteroatoms in the ring structure may also be referred to as "heteroaryl" or "heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl.

The term "heteroarylene" is the divalent moiety of "heteroaryl".

The term "aralkylene" is the divalent moiety of "aralkyl". The term "aralkyl" refers to a radical of the formula —$R^a$-aryl, where $R^a$ is an alkylene as defined above, for example methylene, ethylene and the like. The aryl part is optionally substituted as described above for aryl group.

The term "cycloalkylene" is the divalent moiety of "cycloalkyl". The term "cycloalkyl" refers to monocyclic or polycyclic cycloalkyl radical. Examples of monocyclic a cycloakyl include cyclopropyl, cyclobutyl, cyclopentyl, cyclohexyl, cycloheptyl, and cyclooctyl. Examples of polycyclic cycloalkyl radical include, for example admantyl, nor-bornyl, decalinyl, 7,7-dimethyl-bicyclo[2.2.1]heptanyl, tricyclo[5.2.1.0$^{2,6}$]decyl and the like. Unless otherwise stated specifically in the specification, the term "cycloalkyl" is meant to include monocyclic or polycyclic cycloalkyl radical that are optionally substituted by one or more substituents selected from alkyl, halo, oxo or alkylene chain.

The term "cycloalkylalkylene" refers to group —$R^a$-cycloalkyl-" where $R^a$ is an alkylene as defined above, for example methylene, ethylene and the like. As used herein $C_1$-$C_8$ cycloalkylalkylene refers to a cycloalkyl linked through a $C_1$-$C_8$ alkylene group.

The term "divalent hydrocarbon radical" refers to divalent hydrocarbon radicals having 2 to 18 carbon atoms include alkylene radicals such as ethylene, methyl-methylene, propylene, butylene, pentylene, hexylene and octadecylene; alkylene radicals such as vinylene, allylene and butadienylene; cycloalkylene radicals such as cyclo-butylene, cyclopentylene and cyclohexylene; cycloalkenylene radicals such as cyclopentenylene and cyclohexenylene; arylene radicals such as phenylene and xenylene; aralkylene radicals as benzylene; and alkarylene radicals such as tolylene.

The term "polymerizable moiety" refers to any double bond capable of addition polymerization, in particular free radical polymerization, such as carbon-carbon double bond.

The term "(meth)acrylate" in the context of the present disclosure is meant to refer to the acrylate as well as to the corresponding methacrylate.

The term "(meth)acryl" in the context of the present disclosure is meant to refer to the acryl as well as to the corresponding methacryl.

The present disclosure relates to a dental composition containing a polymerizable compound having at least one optionally derivatized β-hydroxy urethane unit. The polymerizable compound having at least one optionally derivatized β-hydroxy urethane unit is obtained without use of metal and isocyanate and by a reaction between an at least one component A having at least one cyclic carbonate group with an at least one component B having at least one of primary amine functional group and secondary amine functional group. The present disclosure relates to use of the polymerizable compound having at least one optionally derivatized β-hydroxy urethane unit for the preparation of a dental composition, in particular, a dental composite, a glass ionomer, a dental cement, a dental sealant, and a dental adhesive.

The phrase "at least one of filler and solvent" should be understood to mean "only filler", "only solvent", or "both filler and solvent".

In one embodiment, the at least one component A having at least one cyclic carbonate group may be a cyclic carbonate having 5-, 6- or 7-membered ring.

In one embodiment, the at least one component A having at least one cyclic carbonate group is a compound of Formula I:

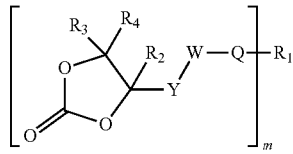

Formula I wherein $R_1$ represents a hydrogen, an m-valent $C_{1-22}$ hydrocarbon group, which group optionally includes 1 to 12 oxygen or sulfur atoms, and which is optionally substituted by $C_{1-4}$ alkyl group or a (meth)acrylate group;

$R_2$, $R_3$ and $R_4$ are independent from each other, and represent a hydrogen or a $C_{1-4}$ alkyl group;

W is an oxygen atom, —O—C=O— or a direct bond;

Q is a direct bond or a straight or branched chain alkylene having 1 to 4 carbons;

Y is a direct bond, an unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group optionally includes at least one of 1-6 oxygen atoms, nitrogen atoms or sulphur atoms; wherein each substituted groups is substituted by $C_{1-4}$ alkyl group; and m is an integer of from 1 to 6.

In a preferred embodiment thereof, $R_1$ is a saturated aliphatic $C_{1-16}$ hydrocarbon chain which optionally contains 2 to 4 oxygen or sulfur atom and which is optionally substituted by $C_{1-4}$ alkyl group, or an unsaturated hydrocarbon having a double bond, which is optionally substituted by $C_{1-4}$ alkyl group.

In formula I, $R_1$ is an m-valent $C_{1-22}$ hydrocarbon group. $R_1$ may be monovalent (m=1), divalent (m=2), trivalent (m=3), tetravalent (m=4), pentavalent (m=5), or hexavalent (m=6). The hydrocarbon group may contain 1 to 12 oxygen atoms in the hydrocarbon group in the form of aliphatic or aromatic ether bonds, keto group, carboxylic acid group, hydroxyl groups or ester group or amide group. The hydrocarbon group may contain 1 to 12 sulfur atoms in the hydrocarbon group in the form of aliphatic or aromatic thioether bonds, thioketone group, thiocarboxylic acid group, thiol groups or thioester group.

In one embodiment of Formula I, $R_1$ may be an unsubstituted or substituted $C_{1-10}$ alkyl group, an unsubstituted or substituted $C_3$-$C_6$ cycloalkyl group, an unsubstituted or substituted $C_1$-$C_8$ cycloalkylalkylene, an unsubstituted or substituted $C_5$-$C_{18}$ aryl group, an unsubstituted or substituted $C_7$-$C_{24}$ aralkyl group, wherein each substituted group may be substituted by one or more of a $C_{1-4}$ alkyl group, a $C_{1-4}$ alkoxy group, a hydroxyl group, an aryl group or an aryloxy group.

In certain embodiments of the dental composition disclosed herein, the compound of Formula I may be di-cyclic carbonate of Formula Ia:

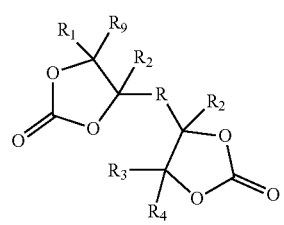

Formula Ia wherein $R_2$, $R_3$ and $R_4$ are as defined above; and

R represents a divalent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or unsubstituted or substituted $C_3$-$C_{18}$ heteroarylene group.

In one embodiment of the dental composition disclosed herein, the compound of Formula I may be mono-cyclic carbonate of Formula Ib:

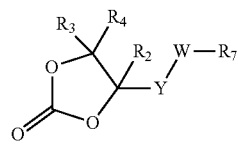

Formula Ib wherein $R_2$, $R_3$, $R_4$, Y and W are as defined above; and $R_7$ is

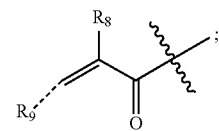

wherein $R^8$ is a hydrogen atom, or a linear $C_{1-3}$ or branched $C_{3-5}$ alkyl group substituted with a COOH group; and $R^9$ is a hydrogen atom, —COOH group, or a linear $C_{1-3}$ or branched $C_{3-5}$ alkyl group substituted with a COOH group;

In another embodiment of the dental composition disclosed herein, the compound of Formula I may be monocyclic carbonate of Formula Ic:

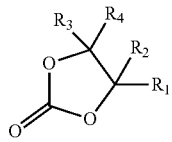

Formula Ic wherein $R_2$, $R_3$ and $R_4$ are as defined above, and $R_1$ is an unsubstituted or substituted $C_{2-10}$ alkyl group, an unsubstituted or substituted $C_3$-$C_6$ cycloalkyl group, an unsubstituted or substituted $C_1$-$C_8$ cycloalkylalkylene, an unsubstituted or substituted $C_5$-$C_{18}$ aryl group, an unsubstituted or substituted $C_7$-$C_{24}$ aralkyl group, wherein each substituted group is substituted by one or more of a $C_{1-4}$ alkyl group, a $C_{1-4}$ alkoxy group, a hydroxyl group, an aryl group or an aryloxy group.

Compound of Formula I may be selected from the following compounds:

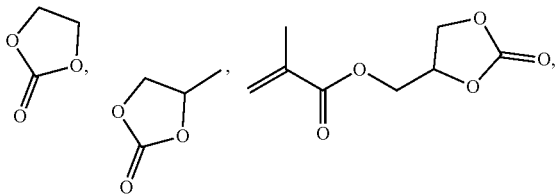

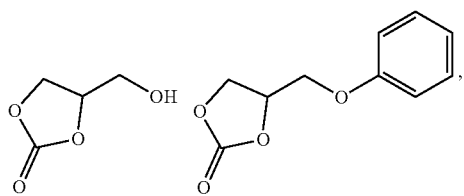

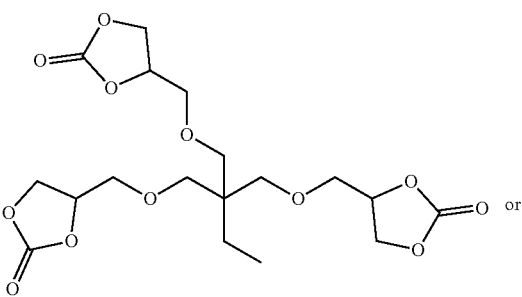 or

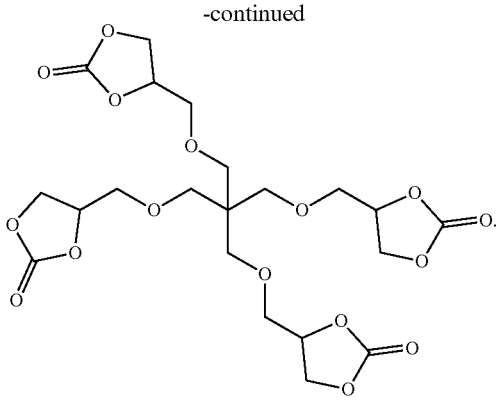

In one embodiment, the at least one component B having at least one of primary amine functional group and secondary amine functional group is a compound of Formula II:

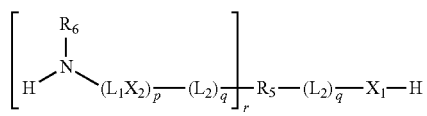

Formula II wherein $R_5$ is a (r+1)-valent aliphatic $C_{2-10}$ group, cycloaliphatic $C_3$-$C_6$ group or an aralkylene group having 7 to 24 carbon atoms, wherein each group optionally contains oxygen or sulfur atoms and which is optionally substituted by $C_{1-4}$ alkyl groups;

$R_6$ is a hydrogen atom, a $C_{1-6}$ alkyl group, a $C_{3-10}$ cycloalkyl group, a $C_7$-$C_{12}$ aralkyl group, or an (meth) acryl group; wherein each group is optionally substituted by one or more of a $C_{1-4}$ alkyl group, a $C_{1-4}$ alkoxy group, or a hydroxyl group;

$L_1$ and $L_2$ are independently a same or different straight or branched chain alkylene having from 1 to 4 carbons;

$X_1$ is a direct bond, an oxygen atom or a nitrogen atom substituted by $R_6$;

$X_2$ is an oxygen atom;

p and q are integer of from 0 to 4; and r is an integer of from 1 to 6.

The phrase "at least one of primary amine functional group and secondary amine functional group" should be understood to mean "only primary amine functional group", "only secondary amine functional group", or "both primary amine functional group and secondary amine functional group".

In one embodiment of Formula II, $R_5$ is a (r+1)-valent aliphatic $C_{2-10}$ group, cycloaliphatic $C_3$-$C_6$ group or an aralkylene group having 7 to 24 carbon atoms. $R_5$ may be divalent (r=1), trivalent (r=2), tetravalent (r=3), pentavalent (r=5), hexavalent (r=5) or heptavalent (r=6).

In certain embodiment of the dental composition disclosed herein, the compound of Formula II may be diamine of Formula IIa:

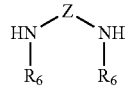

Formula IIa wherein $R_6$ is as defined above; and

Z is divalent aliphatic $C_{2-10}$ group, cycloaliphatic $C_3$-$C_6$ group or an aralkylene group having 7 to 24 carbon atoms, wherein each group optionally contains oxygen or sulfur atoms and which is optionally substituted by $C_{1-4}$ alkyl groups.

In certain embodiment of the dental composition disclosed herein, the compound of Formula II may be compound of Formula IIa:

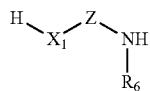

Formula IIb wherein $R_6$, $X_1$ and are as defined above.

In certain embodiment of the dental composition disclosed herein, the compound of Formula II may be mono-amine of Formula IIc:

$$H_2N—R_5$$

Formula IIc wherein $R_5$ is a mono-valent aliphatic $C_{1-10}$ group, cycloaliphatic $C_3$-$C_6$ group or an aralkylene group having 7 to 24 carbon atoms.

In certain embodiment of the dental composition disclosed herein, the compound of Formula II may be amine of Formula IId:

Formula IId wherein $R_5$ and $R_6$ are as defined above.

Compound of Formula II may be selected from ethylene diamine, propylene diamine, butylene diamine, pentamethylene diamine, hexamethylene diamine, heptamethylene diamine, tetramethylene diamine, octamethylene diamine, trimethylhexa-methylenediamine, diethylene triamine, triethylene tetraamine, tetraethylene pentamine, 4,7,10-trioxa-1,13-tridecane diamine, 2,2'-ethylenedioxy) diethylamine, 1,3-bis-(aminomethyl) cyclohexane, 1,3-bis-(4-aminophenoxy)benzene, 4,4'-methylene bis-cyclohexylamine, 5-amino-1,3,3-trimethylcyclohexanemethylamine, Jeffamine T403, Jeffamine T3000, Jeffamine T5000, amino alcohol, propanol amine, N,N'-dimethyl ethylene diamine, N,N'-dibenzyl ethylene diamine, N,N'-dibenzyl 5-oxanonane diamine-1,9, N,N'-dibenzyl 3,6-dioxaoctane diamine-1,8, N,N'-diethyl propane diamine, N,N'dimethyl propylene diamine, n-butylamine, hexylamine, cyclohexylamine, or benzylamine.

In one embodiment of the dental composition disclosed herein, the polymerizable compound having at least one optionally derivatized β-hydroxy urethane unit may be present in an amount of from 1 to 99% based on total weight of the dental composition. Alternatively, in the range of from 2 to 95%; alternatively, in the range of from 5 to 90% or any value, range, or sub-range there between, based on the total weight of the dental composition.

In one embodiment, when step (ii) is present, then the at least one unsaturated mono- or poly-carboxylic acid is selected from the group consisting of acrylic acid, (meth) acrylic acid, itaconic acid, maleic acid and fumaric acid.

In one embodiment, when step (ii) is present, then the intermediate compound having at least one β-hydroxy urethane unit and the residual —NH or —OH group is one of Formula:

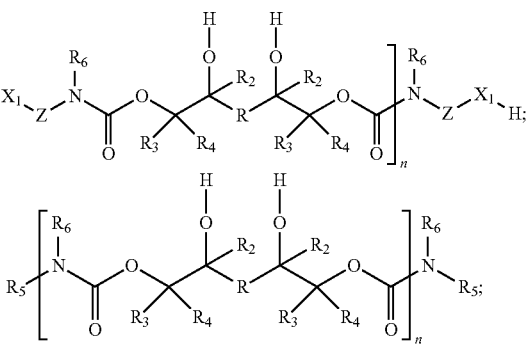

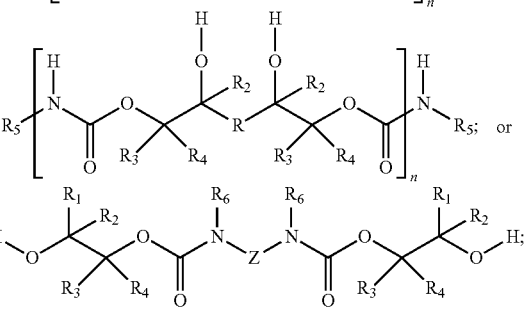

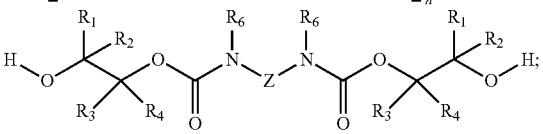

wherein

R represents a divalent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or unsubstituted or substituted $C_3$-$C_{18}$ heteroarylene group;

$R_1$ is an unsubstituted or substituted $C_{2-10}$ alkyl group, an unsubstituted or substituted $C_3$-$C_6$ cycloalkyl group, an unsubstituted or substituted $C_1$-$C_8$ cycloalkylalkylene, an unsubstituted or substituted $C_5$-$C_{18}$ aryl group, an unsubstituted or substituted $C_7$-$C_{24}$ aralkyl group, wherein each substituted group is substituted by one or more of a $C_{1-4}$ alkyl group, a $C_{1-4}$ alkoxy group, a hydroxyl group, an aryl group or an aryloxy group;

$R_2$, $R_3$ and $R_4$ are independent from each other, and represent a hydrogen or a $C_{1-4}$ alkyl group;

Z is a divalent aliphatic $C_{2-10}$ group, a divalent cycloaliphatic $C_3$-$C_6$ group or an aralkylene group having 7 to 24 carbon atoms, wherein each group optionally contain oxygen atoms and which is optionally substituted by $C_{1-4}$ alkyl group;

$R_5$ is a mono-valent aliphatic $C_{1-10}$ group, cycloaliphatic $C_3$-$C_6$ group or an aralkylene group having 7 to 24 carbon atoms;

$R_6$ is a hydrogen atom, a $C_{1-6}$ alkyl group, a $C_{3-10}$ cycloalkyl group, a $C_7$-$C_{12}$ aralkyl group, or an (meth) acryl group; wherein each group is optionally substituted by one or more of a $C_{1-4}$ alkyl group, a $C_{1-4}$ alkoxy group, or a hydroxyl group; $X_1$ is an oxygen atom or a nitrogen atom substituted by $R_6$; and n is an integer of from 1 to 5.

In one embodiment, the composition further comprises a polymerizable monomer.

In one embodiment, the composition further comprises a polymerization initiator, preferably a thermal initiator, a redox initiator or a photoinitiator.

In one embodiment, the polymerization initiator is present in an amount of from 0.1 to 5% w/w based on total weight of the dental composition.

In one embodiment, the at least one filler is present in an amount of from 0.5 to 85% w/w based on total weight of the dental composition.

In one embodiment, the dental composition is selected from the group consisting of a dental composite, a glass ionomer, dental cement, dental sealant, and dental adhesive.

The object of the present invention is also solved by an inventive process for preparing a polymerizable compound having at least one optionally derivatized β-hydroxy urethane unit, which are represented by the following formula IIIa-IIIc:

Formula IIIa

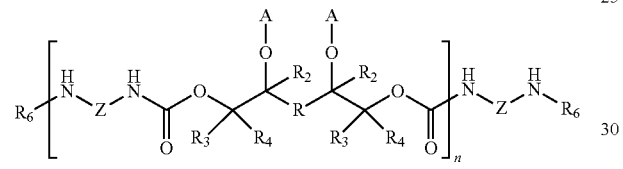

Formula IIIb

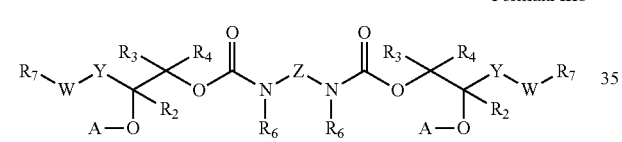

Formula IIIc

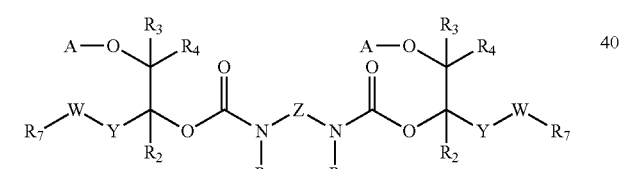

wherein

R represents a divalent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or unsubstituted or substituted $C_3$-$C_{18}$ heteroarylene group;

$R_2$, $R_3$ and $R_4$ are independent from each other, and represent a hydrogen or a $C_{1-4}$ alkyl group;

Z is a divalent aliphatic $C_{2-10}$ group, a divalent cycloaliphatic $C_3$-$C_6$ group or an aralkylene group having 7 to 24 carbon atoms, wherein each group optionally contain oxygen atoms and which is optionally substituted by $C_{1-4}$ alkyl group;

$R_6$ is a hydrogen atom, a $C_{1-6}$ alkyl group, a $C_{3-10}$ cycloalkyl group, a $C_7$-$C_{12}$ aralkyl group, or an (meth) acryl group; wherein each group is optionally substituted by one or more of a $C_{1-4}$ alkyl group, a Cia alkoxy group, or a hydroxyl group;

$R_7$ is

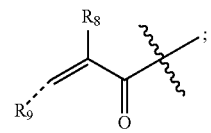

wherein $R^8$ is a hydrogen atom, or a linear $C_{1-3}$ or branched $C_{3-5}$ alkyl group substituted with a COOH group;

$R_9$ is a hydrogen atom, —COOH group, or a linear $C_{1-3}$ or branched $C_{3-5}$ alkyl group substituted with a COOH group;

A is independently same or different and is a hydrogen atom or $R_7$; W is an oxygen atom; Y is $C_1$-$C_4$ alkylene; and n is an integer of from 1 to 5;

said process comprising the step of reacting an at least one component A having at least one cyclic carbonate group with an at least one component B having at least one of primary amine functional group and secondary amine functional group to form the polymerizable compound having at least one β-hydroxy urethane unit, wherein the at least one component A having at least one cyclic carbonate group is a compound of Formula I:

Formula I

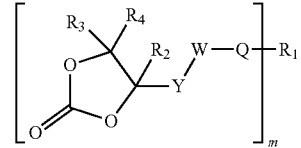

wherein $R_1$ represents a hydrogen, an m-valent $C_{1-22}$ hydrocarbon group, which group optionally includes 1 to 12 oxygen or sulfur atoms, and which is optionally substituted by $C_{1-4}$ alkyl group or a (meth)acrylate group;

$R_2$, $R_3$ and $R_4$ are independent from each other, and represent a hydrogen or a $C_{1-4}$ alkyl group;

W is an oxygen atom, —O—C=O— or a direct bond;

Q is a direct bond or a straight or branched chain alkylene having 1 to 4 carbons;

Y is a direct bond, an unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group optionally includes at least one of 1-6 oxygen atoms, nitrogen atoms or sulphur atoms; wherein each substituted groups is substituted by $C_{1-4}$ alkyl group;

m is an integer of from 1 to 6, wherein the at least one component B having at least one of primary amine functional group and secondary amine functional group is a compound of Formula II:

Formula II

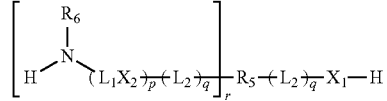

wherein
R$_5$ is a (r+1)-valent aliphatic C$_{2-10}$ group, cycloaliphatic C$_3$-C$_6$ group or an aralkylene group having 7 to 24 carbon atoms, wherein each group optionally contains oxygen or sulfur atoms and which is optionally substituted by C$_{1-4}$ alkyl groups;

R$_6$ is a hydrogen atom, a C$_{1-6}$ alkyl group, a C$_{3-10}$ cycloalkyl group, a C$_7$-C$_{12}$ aralkyl group, or an (meth) acryl group; wherein each group is optionally substituted by one or more of a C$_{1-4}$ alkyl group, a C$_{1-4}$ alkoxy group, or a hydroxyl group;

L$_1$ and L$_2$ are independently a same or different straight or branched chain alkylene having from 1 to 4 carbons;

X$_1$ is a direct bond, an oxygen atom or a nitrogen atom substituted by R$_6$;

X$_2$ is an oxygen atom; p and q are integer of from 0 to 4; and r is an integer of from 1 to 6.

In an aspect of the present disclosure, a method of preparing the polymerizable compound having at least one optionally derivatized β-hydroxy urethane unit are described.

In one embodiment of dental composition disclosed herein, the polymerizable compound having at least one optionally derivatized β-hydroxy urethane unit may be prepared in a single step as shown in Scheme-1

Scheme-1

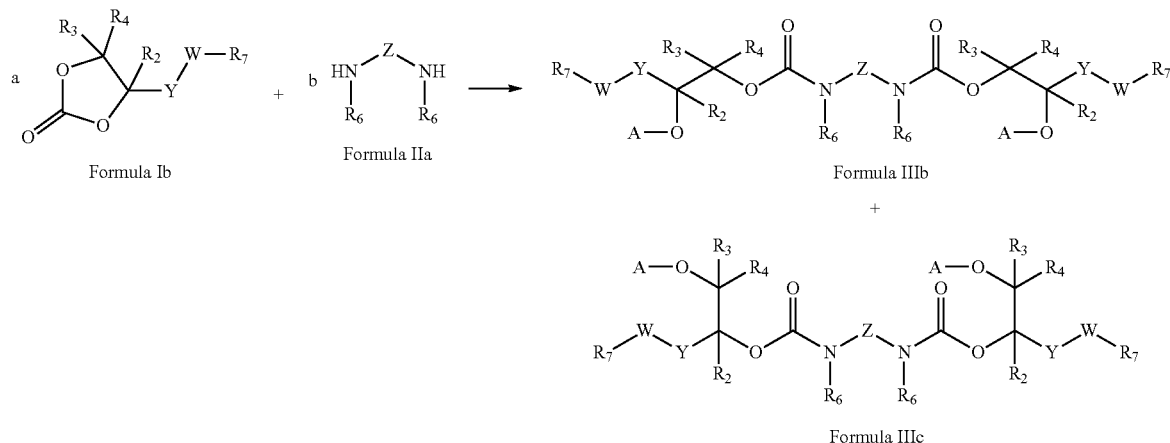

wherein R$_2$, R$_3$, R$_4$, Z, R$_6$, R$_7$, W, Y are as defined above; and A is a hydrogen atom.

As shown in Scheme-1, a equivalent of compound of Formula Ib and b equivalent of compound of Formula IIa may be dissolved in a solvent and stirred at a reaction temperature.

In some embodiments of the method of preparing the polymerizable compound having at least one optionally derivatized β-hydroxy urethane unit, a polymerization inhibitor may be included to prevent the polymerizable moiety from premature polymerization.

In certain embodiments of the method of preparing the polymerizable compound having at least one optionally derivatized β-hydroxy urethane unit, the polymerization inhibitor is selected from the group consisting of butylated hydroxyl toluene (BHT), (2,2,6,6-Tetramethylpiperidin-1-yl)oxyl (TEMPO), phenothiazine and galvinoxyl radical.

The polymerization inhibitor may be present in an amount of from 0.01 mol % to 0.5 mol % based on total moles of compound of Formula Ib.

In some embodiments of the method of preparing the polymerizable compound having at least one optionally derivatized β-hydroxy urethane unit, the solvent is selected from the group consisting of tetrahydrofuran, dioxane, toluene, methanol, ethanol, n-propanol, iso-propanol, n-butanol, sec-butanol, tert-butanol, dimethylsulphoxide (DMSO), and N,N-dimethylformamide (DMF).

The reaction temperature may be, for example from 20° C. to 60° C., such as from 30° C. to 55° C.

In certain embodiments of the dental composition, the polymerizable compound having at least one optionally derivatized β-hydroxy urethane unit may be prepared in a single step as shown in Scheme-2 below:

Scheme-2

[Chemical scheme showing Formula Ia (di-cyclic carbonate) + Formula IIb* (H₂N-Z-NH-R₆) → Formula IIIa]

wherein $R_2$, $R_3$, $R_4$, $R$, $Z$, $R_6$ are as defined above and A is a hydrogen atom.

As shown in Scheme-2, c equivalent of a di-cyclic carbonate of Formula Ia and d equivalent of compound of Formula IIb* may be dissolved in a solvent and stirred at a reaction temperature to form the polymerizable compound having at least one optionally derivatized β-hydroxy urethane unit of Formula IIIa.

The object of the present invention us also solved in an alternative way by a process for preparing a polymerizable compound having at least one optionally derivatized β-hydroxy urethane unit, which are represented by the following formula IIId-IIIg:

[Formula IIId]

[Formula IIIe]

[Formula IIIf]

[Formula IIIg]

wherein

R represents a divalent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or unsubstituted or substituted $C_3$-$C_{18}$ heteroarylene group;

$R_1$ is an unsubstituted or substituted $C_{2-10}$ alkyl group, an unsubstituted or substituted $C_3$-$C_8$ cycloalkyl group, an unsubstituted or substituted $C_1$-$C_8$ cycloalkylalkylene, an unsubstituted or substituted $C_5$-$C_{18}$ aryl group, an unsubstituted or substituted $C_7$-$C_{24}$ aralkyl group, wherein each substituted group is substituted by one or more of a $C_{1-4}$ alkyl group, a $C_{1-4}$ alkoxy group, a hydroxyl group, an aryl group or an aryloxy group;

$R_2$, $R_3$ and $R_4$ are independent from each other, and represent a hydrogen or a $C_{1-4}$ alkyl group;

Z is a divalent aliphatic $C_{2-10}$ group, a divalent cycloaliphatic $C_3$-$C_6$ group or an aralkylene group having 7 to 24 carbon atoms, wherein each group optionally contain oxygen atoms and which is optionally substituted by $C_{1-4}$ alkyl group;

$R_5$ is a mono-valent aliphatic $C_{1-10}$ group, cycloaliphatic $C_3$-$C_6$ group or an aralkylene group having 7 to 24 carbon atoms;

$R_6$ is a hydrogen atom, a $C_{1-6}$ alkyl group, a $C_{3-10}$ cycloalkyl group, a $C_7$-$C_{12}$ aralkyl group, or an (meth) acryl group; wherein each group is optionally substituted by one or more of a $C_{1-4}$ alkyl group, a $C_{1-4}$ alkoxy group, or a hydroxyl group;

$R_7$ is

[Structure showing $R_8$, $R_9$ on alkene attached to C=O]

wherein $R_8$ is a hydrogen atom, or a linear $C_{1-3}$ or branched $C_{3-5}$ alkyl group substituted with a COOH group;

$R_9$ is a hydrogen atom, —COOH group, or a linear $C_{1-3}$ or branched $C_{3-5}$ alkyl group substituted with a COOH group;

A is independently same or different and is a hydrogen atom or $R_7$.

$X_1$ is an oxygen atom or a nitrogen atom substituted by $R_6$;

n is an integer of from 1 to 5;

said process comprising the step of:
(a) reacting the at least one component A having at least one cyclic carbonate group with an at least one component B having at least one of primary amine functional group and secondary amine functional group to form an intermediate compound having at least one β-hydroxy urethane unit and residual —NH or —OH group; and
(b) reacting the intermediate compound having at least one β-hydroxy urethane unit and residual —NH or —OH group with an at least one unsaturated mono- or poly-carboxylic acid to form polymerizable compound having at least one derivatized β-hydroxy urethane unit.

wherein the at least one component A having at least one cyclic carbonate group is a compound of Formula I:

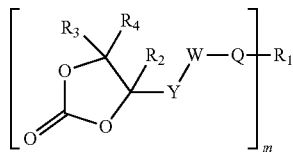

Formula I wherein
$R_1$ represents a hydrogen, an m-valent $C_{1-22}$ hydrocarbon group, which group optionally includes 1 to 12 oxygen or sulfur atoms, and which is optionally substituted by $C_{1-4}$ alkyl group or a (meth)acrylate group;
$R_2$, $R_3$ and $R_4$ are independent from each other, and represent a hydrogen or a $C_{1-4}$ alkyl group;
W is an oxygen atom, —O—C=O— or a direct bond; Q is a direct bond or a straight or branched chain alkylene having 1 to 4 carbons;
Y is a direct bond, an unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group optionally includes at least one of 1-6 oxygen atoms, nitrogen atoms or sulphur atoms; wherein each substituted groups is substituted by $C_{1-4}$ alkyl group;
m is an integer of from 1 to 6,
wherein the at least one component B having at least one of primary amine functional group and secondary amine functional group is a compound of Formula II:

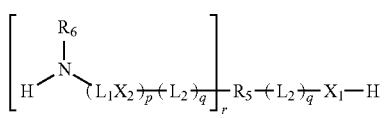

Formula II wherein
$R_5$ is a (r+1)-valent aliphatic $C_{2-10}$ group, cycloaliphatic $C_3$-$C_6$ group or an aralkylene group having 7 to 24 carbon atoms, wherein each group optionally contains oxygen or sulfur atoms and which is optionally substituted by $C_{1-4}$ alkyl groups;
$R_6$ is a hydrogen atom, a $C_{1-6}$ alkyl group, a $C_{3-10}$ cycloalkyl group, a $C_7$-$C_{12}$ aralkyl group, or an (meth)acryl group; wherein each group is optionally substituted by one or more of a $C_{1-4}$ alkyl group, a $C_{1-4}$ alkoxy group, or a hydroxyl group;
$L_1$ and $L_2$ are independently a same or different straight or branched chain alkylene having from 1 to 4 carbons;
$X_1$ is a direct bond, an oxygen atom or a nitrogen atom substituted by $R_6$; $X_2$ is an oxygen atom; p and q are integer of from 0 to 4; and r is an integer of from 1 to 6.
In one embodiment, the at least one unsaturated mono- or poly-carboxylic acid, is selected from the group consisting of acrylic acid, (meth)acrylic acid, itaconic acid, maleic acid and fumaric acid . . .

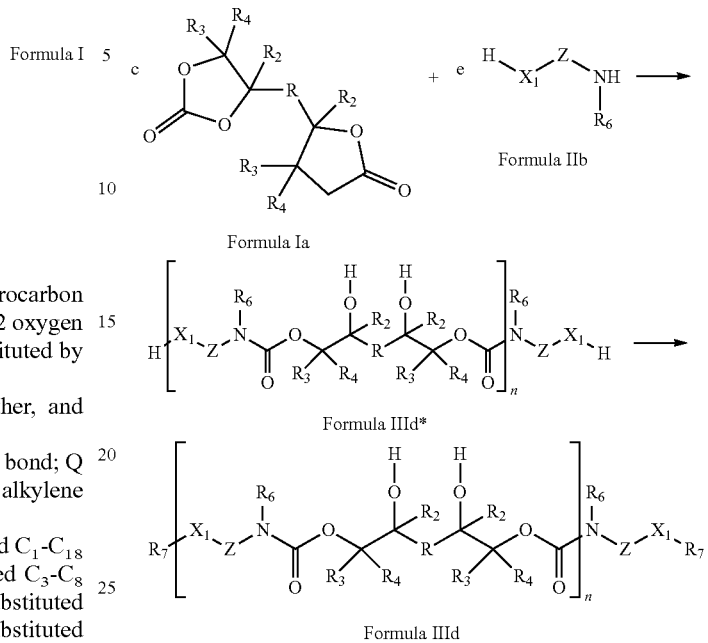

Scheme-3 wherein $R_2$, $R_3$, $R_4$, R, $X_1$, Z, $R_6$, $R_7$ are as defined above; and A is independently same or different and is a hydrogen atom or $R_7$. As depicted in Scheme 3, c equivalent of a di-cyclic carbonate of Formula Ia may react with e equivalent of a compound of Formula IIb to form an intermediate compound of Formula IIId* having at least one β-hydroxy urethane unit and the residual —NH or —OH group. The intermediate compound of Formula IIId* may then react with an at least one unsaturated mono- or poly-carboxylic acid to form the polymerizable compound having at least one optionally derivatized β-hydroxy urethane unit of Formula IIId.

In one particular embodiment, the polymerizable compound having at least one optionally derivatized β-hydroxy urethane unit may be prepared as shown in Scheme 4 below:

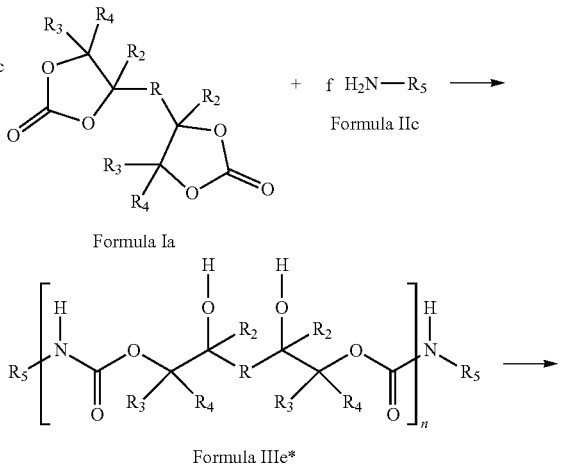

Scheme-4

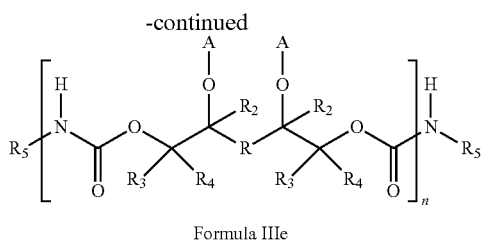

Formula IIIe wherein $R_2$, $R_3$, $R_4$, R, are as defined above; $R_5$ is a mono-valent aliphatic $C_{1-10}$ group, cycloaliphatic $C_3$-$C_6$ group or an aralkylene group having 7 to 24 carbon atoms; A is independently same or different and is the same as $R_7$, wherein $R_7$ is as defined above.

As depicted in Scheme 4, c equivalent of a di-cyclic carbonate of Formula Ia may react with f equivalent of a compound of Formula IIc to form an intermediate compound of Formula IIIe' having at least one β-hydroxy urethane unit and the residual —NH group. The intermediate compound of Formula IIIe* may then react with an at least one unsaturated mono- or poly-carboxylic acid to form the polymerizable compound having at least one optionally derivatized β-hydroxy urethane unit of Formula IIIe. The polymerizable compound may be prepared as shown below in Scheme-5:

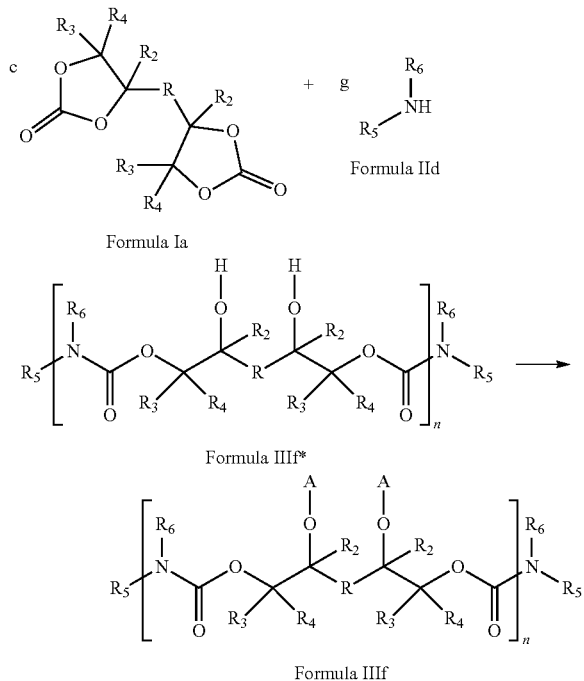

Formula IIIf wherein $R_2$, $R_3$, $R_4$, $R_6$ are as defined above; $R_5$ is a mono-valent aliphatic $C_{1-10}$ group, cycloaliphatic $C_3$-$C_6$ group or an aralkylene group having 7 to 24 carbon atoms and A is independently same or different and is $R_7$, wherein $R_7$ is as defined above.

As depicted in Scheme 5, c equivalent of a di-cyclic carbonate of Formula Ia may react with f equivalent of a compound of Formula IId to form an intermediate compound of Formula IIIf having at least one β-hydroxy ure- thane unit and the residual —NH group. The intermediate compound of Formula IIIf* may then react with an at least one unsaturated mono- or poly-carboxylic acid to form the polymerizable compound having at least one optionally derivatized β-hydroxy urethane unit of Formula IIIf.

In another embodiment, the polymerizable compound having at least one optionally derivatized β-hydroxy urethane unit may be prepared as shown in Scheme 6 below:

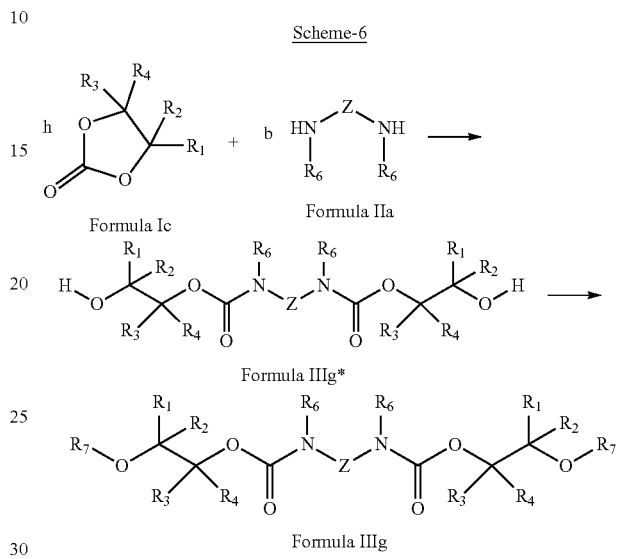

wherein $R_1$, $R_2$, $R_3$, $R_4$, Z, $R_6$, $R_7$ are as defined above.

As depicted in Scheme 6, h equivalent of a mono-cyclic carbonate of Formula Ic may react with b equivalent of a compound of Formula IIa to form an intermediate compound of Formula IIIg* having at least one β-hydroxy urethane unit and the residual —NH or —OH group. The intermediate compound of Formula IIIg* may then react with an at least one unsaturated mono- or poly-carboxylic acid to form the polymerizable compound having at least one optionally derivatized β-hydroxy urethane unit of Formula IIIg.

In one embodiment, the Intermediate compound having at least one β-hydroxy urethane unit and the residual —NH or —OH group is one of Formula:

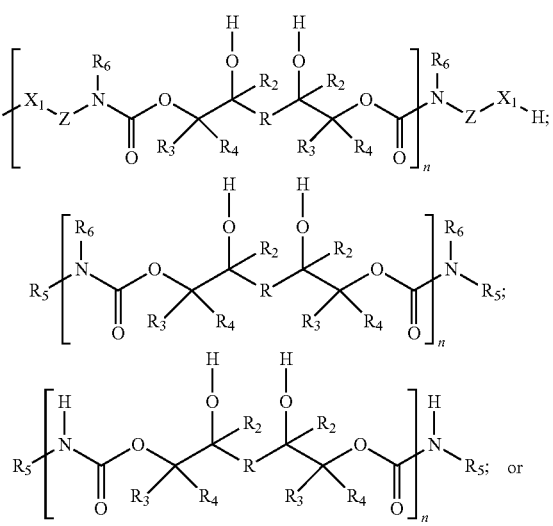

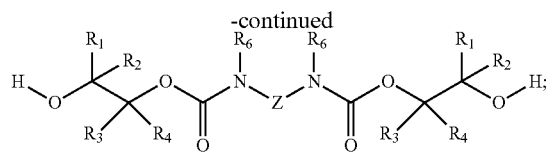

wherein

R represents a divalent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or unsubstituted or substituted $C_3$-$C_{18}$ heteroarylene group;

$R_1$ is an unsubstituted or substituted $C_{2-10}$ alkyl group, an unsubstituted or substituted $C_3$-$C_6$ cycloalkyl group, an unsubstituted or substituted $C_1$-$C_8$ cycloalkylalkylene, an unsubstituted or substituted $C_5$-$C_{18}$ aryl group, an unsubstituted or substituted $C_7$-$C_{24}$ aralkyl group, wherein each substituted group is substituted by one or more of a $C_{1-4}$ alkyl group, a $C_{1-4}$ alkoxy group, a hydroxyl group, an aryl group or an aryloxy group;

$R_2$, $R_3$ and $R_4$ are independent from each other, and represent a hydrogen or a $C_{1-4}$ alkyl group;

Z is a divalent aliphatic $C_{2-10}$ group, a divalent cycloaliphatic $C_3$-$C_6$ group or an aralkylene group having 7 to 24 carbon atoms, wherein each group optionally contain oxygen atoms and which is optionally substituted by $C_{1-4}$ alkyl group;

$R_5$ is a mono-valent aliphatic $C_{1-10}$ group, cycloaliphatic $C_3$-$C_6$ group or an aralkylene group having 7 to 24 carbon atoms;

$R_6$ is a hydrogen atom, a $C_{1-6}$ alkyl group, a $C_{3-10}$ cycloalkyl group, a $C_7$-$C_{12}$ aralkyl group, or an (meth) acryl group; wherein each group is optionally substituted by one or more of a $C_{1-4}$ alkyl group, a $C_{1-4}$ alkoxy group, or a hydroxyl group;

$X_1$ is an oxygen atom or a nitrogen atom substituted by $R_6$; and n is an integer of from 1 to 5.

The Filler

The dental composition of the present disclosure may include fillers.

Examples of suitable filler particles include, but are not limited to, strontium silicate, strontium borosilicate, barium silicate, barium borosilicate, barium fluoroalumino borosilicate glass, barium alumino borosilicate, calcium silicate, calcium alumino sodium fluoro phosphor-silicate lanthanum silicate, alumino silicate, and the combination comprising at least one of the foregoing fillers. The filler particles can further comprise silicon nitrides, titanium dioxide, fumed silica, colloidal silica, quartz, kaolin ceramics, calcium hydroxy apatite, zirconia, and mixtures thereof. Examples of fumed silica include OX-50 from DeGussa AG (having an average particle size of 40 nm), Aerosil R-972 from DeGussa AG (having an average particle size of 16 nm), Aerosil 9200 from DeGussa AG (having an average particle size of 20 nm), other Aerosil fumed silica might include Aerosil 90, Aerosil 150, Aerosil 200, Aerosil 300, Aerosil 380, Aerosil R711, Aerosil R7200, and Aerosil R8200, and Cab-O-Sil M5, Cab-O-Sil TS-720, Cab-O-Sil TS-610 from Cabot Corp.

The filler particles used in the composition disclosed herein may be surface treated before they are blended with organic compounds. The surface treatment using silane coupling agents or other compounds are beneficial as they enable the filler particles to be more uniformly dispersed in the organic resin matrix, and also improve physical and mechanical properties. Suitable silane coupling agents include 3-methacryloxy-propyltrimethoxysilane, methacryloxyoctyltrimethoxysilane, styrylethyltrimethoxsilane, 3-mercaptopropyltrimethoxysilane, and mixtures thereof.

The filler particles can have a particle size of from about 0.002 microns to about 25 microns. In one embodiment, the filler can comprise a mixture of a micron-sized radiopaque filler such as barium alumino fluoro borosilicate glass (BAFG, having an average particle size of about 1 micron) with nanofiller particles, such as fumed silica such as OX-50 from Degussa AG (having an average particle size of about 40 nm). The concentration of micron-size glass particles can range from about 50 weight percent to about 75 weight percent of the cement composition, and the nano-size filler particles can range from about 1 weight percent to about 20 weight percent of the cement composition.

The dental composition of the present disclosure may include the at least one filler in an amount of from 0.5 to 85% w/w based on total weight of the dental composition.

The dental composition of the present disclosure may be a composite, and may include a filler material in an amount from about 30 to about 85 percent by weight.

The dental composition of the present disclosure may be an adhesive, and may include a filler in an amount from about 50 to about 65 percent by weight.

The dental composition of the present disclosure may be a sealant, and may include filler in an amount from about 10 to about 50 percent by weight.

A dental composition according to the disclosure may be a cement, and may include filler in an amount from about 50 to about 85 percent by weight.

The Initiators

Initiators are often used in chain-growth polymerization such as radical polymerization to regulate initiation by heat or light.

Thermal polymerization initiators are compounds that generate radicals or cat-ions upon exposure to heat. For example, azo compounds such as 2,2'-azobis(isobutyronitrile) (AIBN) and organic peroxides such as benzoyl peroxide (BPO) are well-known thermal radical initiators, and benzenesulfonic acid esters and alkylsulfonium salts have been developed as thermal cation initiators. Organic and inorganic compounds can be used to generate radicals that initiate polymerizations. Radicals may be generated by thermal or ambient redox conditions. Decomposition rates for some initiators vary with pH and the presence of amines.

Additional free radical initiators may include organic photoinitiators. Suitable photoinitiators include Type I and Type II. They can be used independently or as mixture of different photoinitiators plus additional co-initiators. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate as the accelerator.

Other suitable photoinitiators for polymerizing free radically photopolymerizable compositions may include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm may include 1-hydroxy cyclohexyl phenyl ketone (IRGACURE 184), 2,2-di-methoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl) butanone (IRGACURE 369), 2-methyl-1-[4-(methyl-thio) phenyl]-2-morpholinopropan-1-one (IRGACURE 907), and 2-hydroxy-2-methyl-1-phenyl propan-1-one (DAROCUR 1173). bis(2,4,6-trimethylbenzoyl) phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X).

In one embodiment of the dental composition, the initiator may be present in an amount of from 0.1 weight percent to about 5 weight percent of the dental composition.

Polymerizable Monomer

In one embodiment of the dental composition, the polymerizable monomer may be present in an amount of from 10 weight percent to about 95 weight percent of the dental composition.

Polymerizable monomer may be selected from the group consisting of acrylates, methacrylates, ethylenically unsaturated compounds, carboxyl group-containing unsaturated monomers, $C_{2-8}$ hydroxyl alkyl esters of (meth)acrylic acid, $C_{1-24}$ alkyl esters or cycloalkyl esters of (meth)acrylic acid, $C_{2-18}$ alkoxyalkyl esters of (meth)acrylic acid, olefins or diene compounds, monoesters/diesters, monoethers, adducts, TPH resin, SDR Resin and/or BPA-free resins.

Examples of specific acrylate monomer include but are not limited to ethyl acrylate, propyl acrylate, isopropyl acrylate, 2-hydroxyethyl acrylate, hydroxypropyl acrylate, tetrahydrofurfuryl acrylate, glycidyl acrylate, glycerol mono- and di-acrylate, ethyleneglycol diacrylate, polyethyleneglycol diacrylate, neopentyl glycol diacrylate, trimethylolpropane triacrylate, mono-, di-, tri-acrylate, mono-, di-, tri-, and tetra-acrylates of pentacrythritol and dipentaerythritol, 1,3-butanediol diacrylate, 1,4-butanedioldiacrylate, 1,6-hexane diol diacrylate, 2,2'-bis[3(4-phenoxy)-2-hydroxypropane-1-acrylate]propane, 2,2'bis(4-acryloxyphenyl)propane. 2,2'-bis[3(4-phenoxy)-2-hydroxy-propane-1-acrylate]propane, dipentaerthritol pentaacrylate esters and dipentaerthritol pentaacrylate esters.

Examples of specific conventional methacrylate monomer include but are not limited to methacrylates, ethyl methacrylate, propyl methacrylate, isopropyl methacrylate, tetrahydrofurfuryl methacrylate, glycidyl methacrylate, the diglycidyl methacrylate of bis-phenol A (2,2-Bis[4-(2-hydroxy-3-methacryloxypropoxy)phenyl]propane) (BisGMA), glycerol mono- and di-methacrylate, ethyleneglycol dimethacrylate, polyethyleneglycol dimethacrylate, triethylene glycol dimethacrylate (TEGDMA), neopentylglycol dimethacrylate, trimethylol propane trimethacrylate, mono-, di-, tri-, and tetra-methacrylates of pentacrythritol and dipentaerythritol, 1,3-butanediol dimethacrylate, 1,4-butanediol di-methacrylate, Bis[2-(methacryloyloxy)ethyl]phosphate (BisMEP), l,6-hexanediol di-methacrylate, 2-2'-bis(4-methacryloxyphenyl)propane, 2,2'-bis[4(2-hydroxy-3-methacryloxyphenyl)]propane, 2,2' bis[4(2-hydroxy-3acryloxyphenyl)propane, 2,2'-bis(4-methacryloxyethoxyphenyl) propane, 2,2'-bis(4-acryloxyethoxyphenyl)propane, 2,2'-bis (4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane.

Examples of ethylenically unsaturated compounds include but are not limited to acrylic acid esters, methacrylic acid esters, hydroxy-functional acrylic acid esters, hydroxy-functional methacrylic acid esters, halogen and hydroxy containing methacrylic acid esters and combinations thereof. Such free radically polymerizable compounds include mono-, di- or poly-(meth)acrylates (i.e., acrylates and methacrylates) such as, methyl(meth)acrylate, ethyl(meth)acrylate, isopropyl (meth)acrylate, n-hexyl(meth)acrylate, stearyl(meth)acrylate, allyl(meth)acrylate, glycerol tri (meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethyl-methane, ethoxylated bisphenol A di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth) acrylamide; urethane (meth)acrylates; the bis-(meth) acrylates of polyethylene glycols, and chlorine-, bromine-, fluorine-, and hydroxyl group containing monomers, for example, 3-chloro-2-hydroxylpropyl (meth)acrylate.

Examples of carboxyl group-containing unsaturated monomers include but are not limited to such as acrylic acid, methacrylic acid, crotonic acid, itaconic acid, maleic acid, and fumaric acid.

Examples of $C_{2-8}$ hydroxyl alkyl esters of (meth)acrylic acid include but are not limited to 2-hydroxylethyl (meth) acrylate, 2-hydroxypropyl (meth)acrylate, 3-hydroxypropyl (meth)acrylate, and hydroxybutyl (meth)acrylate.

Examples of $C_{1-24}$ alkyl esters or cycloalkyl esters of (meth)acrylic acid include but are not limited to, methyl methacrylate, ethyl methacrylate, propyl methacrylate, isopropyl methacrylate, n-, sec-, or t-butyl methacrylate, hexyl methacrylate, 2-ethylhexyl methacrylate, octylmethacrylate, decyl methacrylate, lauryl methacrylate, stearyl methacrylate, and cyclohexyl methacrylate.

Examples of $C_{2-18}$ alkoxyalkyl esters of (meth)acrylic acid include but are not limited to methoxybutyl methacrylate, methoxyethyl methacrylate, ethoxyethyl methacrylate, and ethoxybutyl methacrylate.

Olefins or diene compounds include but are not limited to ethylene, propylene, butylene, isobutene, isoprene, chloropropene, fluorine containing olefins and vinyl chloride.

Examples of monoesters may include monoesters between a polyether polyol (e.g., polyethylene glycol, polypropylene glycol or polybutylene glycol) and an unsaturated carboxylic acid (preferably methacrylic acid), monoesters or diesters between an acid anhydride group-containing unsaturated compounds (e.g., maleic anhydride or itaconic anhydride) and a glycol (e.g. ethylene glycol, 1,6-hexanediol or neopentyl glycol).

Examples of monoethers may include monoethers between a polyether polyol (e.g., polyethylene glycol, polypropylene glycol or polybutylene glycol) and a hydroxyl group-containing unsaturated monomers (e.g., 2-hydroxyl methacrylate).

Examples of adducts may include but are not limited to adducts between an unsaturated carboxylic acid and a monoepoxy compound; adducts between glycidyl (meth) acrylates (preferably methacrylate) and a monobasic acid (e.g., acetic acid, propionic acid, p-t-butylbenzonic acid or a fatty acid).

In formulated compositions, additional additives may be optionally included: ultra-violet stabilizers, fluorescent agents, opalescent agents, pigments, viscosity modifiers, fluoride-releasing agents, polymerization inhibitors, and the like. Typical polymerization inhibitors for a free radical system may include hydroquinone monomethyl ether (MEHQ), butylated hydroxytoluene (BHT), tertiary butyl hydro quinine (TBHQ), hydroquinone, phenol, butyl hydroxyaniline, and the like. The inhibitors act as free radical scavengers to trap free radicals in the composition and to extend the shelf life stability of the composition. The polymerization inhibitors, if present, may be present in amounts of from about 0.001 weight percent to about 1.5 weight percent of the dental composition, such as from about 0.005 weight percent to about 1.1 weight percent or from about 0.01 weight percent to about 0.08 weight percent of dental composition. The composition may include one or more polymerization inhibitors.

Depending upon the application of the dental composition and the manner in which polymerization is achieved, various components of the cement may be packaged differently. For example, in the case of a redox-based system, ingredients of the dental composition are divided into two separate packages—the first package containing the copolymer, comonomer, the initiator and water, and the second package containing the reactive filler and the activator. In another embodiment, the first package contains all solid materials (e.g., copolymer, comonomer, reactive filler) and if desired, the reducing agent, and the second package contains water and if desired, the initiator. In the case of photo-initiation, the photo-initiator can be included in either the solid (e. g. paste) or liquid parts of the dental composition.

In one embodiment of the disclosure, the composition is provided as a paste-like material in a single package.

The dental adhesive may be in the form of a self-priming adhesive which further contains a at least one of solvent. The at least one of solvent is selected from the group of consisting of water, ethanol, i-propanol, n-propanol, n-butanol, sec. butanol, tert. butanol, acetone, methyl ethyl ketone and mixtures thereof.

In one embodiment of dental composition, the at least one of solvent is present in an amount of from 0 to 70% w/w based on total weight of the dental composition.

The composition according to the present disclosure may be a one component adhesive composition or a two-pack system adapted to provide adhesive composition upon mixing of the packs. In a two-pack system, the initiator, co-initiator and inhibitor are preferably separated from the polymerizable component of the composition to facilitate chemical curing alone or combined with curing upon exposure to actinic light to provide a dual-cure mode of polymerization. Examples of substances which facilitate self-curing of dental adhesives include for example, BPO, DHEPT and aromatic sulfinic acid salts.

The following non-limiting examples are provided to illustrate an embodiment of the present invention and to facilitate understanding of the invention but are not intended to limit the scope of the invention, which is defined by the claims appended hereto.

EXAMPLES

Synthesis of TMH-HUDMA 0.5961 g (3.766 mmol) TMHDA (CAS 25620-58-0), 1.4022 g (7.532 mmol) 2-Methyl-2-propenoic acid (2-oxo-1,3-dioxolan-4-yl) methyl ester (CAS 13818-44-5) and 0.0017 g (0.0075 mmol) BHT (butylhydroxytoluene) were dissolved together in 10 ml THF and stirred for 6 h at 40° C. Thereafter, THF was distilled of in vacuum. It was obtained 1.998 g (3.766 mmol) of a slightly yellow high viscous liquid. $M_n$=530.61 g/mol.

Application Example 1

15 g of the TMH-HUDMA according to Example 1, 9 g of triethyleneglycol di-methacrylate (TGDMA), 75.00 g of a barium-alumosilicate glass, 0.50 g of camphor qui-none and 0.5 g of diethylaminobenzoic acid ethylester are mixed to form a dental restorative material. The dental restorative material is put into the cavity. Visible light is applied to the dental restorative material to form a polymeric dental restorative having a flexural strength tested according to ISO 4049 of 110 MPa, an E-modulus of 8 GPa and polymerization shrinkage of $\Delta V$=2.3%.

Synthesis of a Reaction Product (A) of DMPDA and Ethylene Carbonate

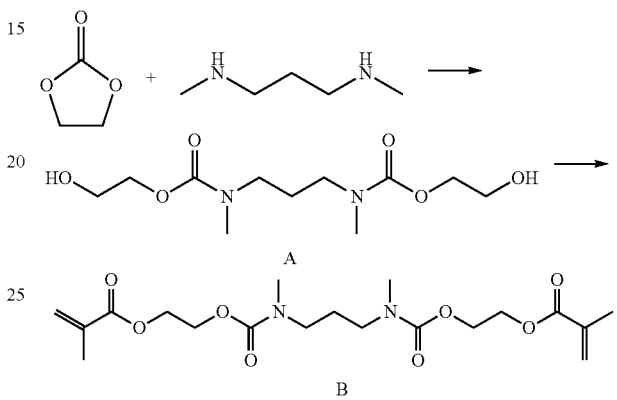

Under inert conditions, 10.0 g (97.9 mmol) of N, N'-dimethyl-1,3-propanediamine DMPDA are initially charged with 17.4 g (196.4 mmol) of ethylene carbonate (CAS 96-49-1). The mixture is then stirred at 80° C. for 47 h. The product A remains as a yellow oil. It is NMR clean and is reacted without further purification. Yield: 26.9 g (96.7 mmol, 99%)

Synthesis of DMPDA-HUDMA (B)

13.1 g (47.1 mmol) A, 33.7 mL (226.1 mmol) freshly distilled methacrylic anhydride, 345 mg (2.8 mmol) DMAP (4-dimethylaminopyridine) and 62 mg (0.28 mmol) BHT are dissolved in 70 mL pyridine (stored over KOH). The mixture is then stirred at 50° C. for 17 h. The orange reaction mixture is diluted with 300 mL DCM (dichloromethane) and washed with 1 M HCl (2×150 mL) and water (150 mL). The organic phase is dried over $Na_2SO_4$ and the solvent is removed in vacuo. It is then dried at 80° C. and a pressure of $2 \times 10^{-2}$ mbar. The crude product (red, gel-like solid) is dissolved in 100 ml of ethyl acetate and 100 ml of sat. $NaHCO_3$ solution and stirred at room temperature for 4 days. Subsequently, the mixture is mixed with 300 ml of water and extracted with DCM (3×300 ml). The combined organic phases are dried over $MgSO_4$ and the solvent is removed in vacuo. After drying under high vacuum, the product B remains as an orange oil.

Yield: 13.5 g (32.6 mmol, 69%).
$M_n$=414.46 g/mol
$n_{20}^D$=1.479

Application Example 2 and Comparative Example 1

Preparation of the Liquids

The used raw materials summarized in Table 1 were weighted in and mixed homogeneously with a magnetic stirrer, at 23° C.

TABLE 1

| | | | Application Example 2 | | Comparative Example 1 | |
|---|---|---|---|---|---|---|
| Raw material | CAS | Molecular mass g/mol | Weight g | Weight content wt-% | Weight g | Weight content wt-% |
| TCB Resin | — | 458.41 | 2.3 | 22.68 | 2.3 | 22.68 |
| UDMA Resin | 105883-40-7 | 498 | — | — | 2.8 | 27.61 |
| HUDMA (B) | — | 414.46 | 2.8 | 27.61 | — | — |
| Trimethylolpropane tri-methacrylate | 3290-92-4 | 338.4 | 0.7 | 6.90 | 0.7 | 6.90 |
| Triethylenglycol dimethacrylate | 109-16-0 | 286.3 | 0.7 | 6.90 | 0.7 | 6.90 |
| Ethoxylated Bisphenol-A-Dimethacrylate | — | 496.58 | 3.4 | 33.52 | 3.4 | 33.52 |
| BHT | 128-37-0 | 220.35 | 0.081 | 0.80 | 0.081 | 0.80 |
| 2-Hydroxy-4-methoxybenzophenone | 131-57-7 | 228.2 | 0.05 | 0.49 | 0.05 | 0.49 |
| Campherchinone | 10373-78-1 | 166.22 | 0.031 | 0.31 | 0.031 | 0.31 |
| Dimethylaminobenzoic acid ethylester | 10287-53-3 | 193.25 | 0.081 | 0.80 | 0.081 | 0.80 |
| Sum | — | — | 10.143 | 100.00 | 10.143 | 100.00 |
| Flexural strength/MPa | | | 98.9 ± 17.8 | | 102.7 ± 5.8 | |
| Refractive Index | | | 1.5117 | | 1.5004 | |
| Viscosity/Pa * s | | | 0.94 | | 3.84 | |

This result shows a significant decrease in the finally achieved viscosity. This is highly advantageous because the final product stays thereby more liquid which enables the skilled user to make use of higher amounts of fillers without risking that the final product becomes too viscous. This would hamper the application largely. The possibility of using higher amounts of fillers enables influencing the mechanical and thermodynamic properties of the final product in a desired and required way.

Application Example 3 and Comparative Example 2

Application Example 3

8.26 g (80 mol-%) EBPADMA, 1.74 g (20 mol-%) HUDMA (B), 0.0017 g Campherchinone and 0.0024 g Dimethylamino benzoic acid ethylester were homogeneously mixed by a magnetic stirrer overnight.

Comparative Example 2

8.09 g (80 mol-%) EBPADMA, 1.91 g (20 mol-%) UDMA Resin, 0.0016 g Campherchinone and 0.0023 g Dimethylamino benzoic acid ethylester were homogeneously mixed by a magnetic stirrer overnight.

The results for the measurement of flexural strength, refractive index and viscosity are summarized in Table 2.

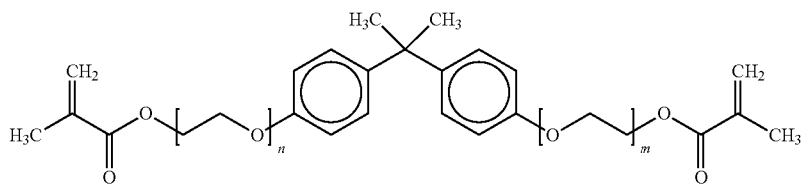

n + m = 3
EBPADMA

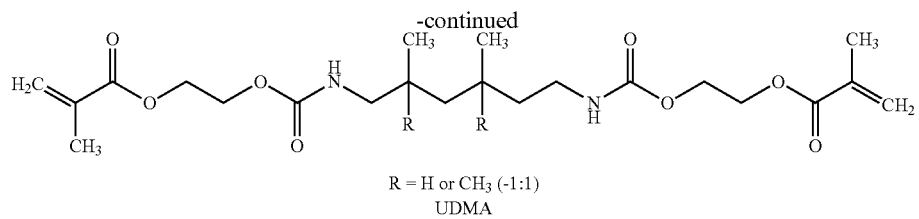

R = H or CH₃ (-1:1)
UDMA

TABLE 2

Application Example 3 and Comparative Example 2

| Raw material | CAS | Molecular mass g/mol | Application Example 3 Mol mol-% | Comparative Example 2 Mol mol-% |
|---|---|---|---|---|
| EBPADMA | — | — | 80 | 80 |
| UDMA Resin | 105883-40-7 | 498 | — | 20 |
| HUDMA (B) | — | 414.46 | 20 | — |
| Flexural strength/MPa | | | 100 | 80 |
| Refractive Index | | | 1.5294 | 1.5295 |
| Viscosity/Pa*s | | | 0.86 | 1.59 |

Application Example 4 and Comparative Example 3

Application Example 4

6.72 g of photocurable methacrylate-based monomer mixture as it is known in the art were mixed with 1.68 g of HUDMA (B). The methacrylate resin was then compounded with 21.60 g of a dental glass mixture. To improve extrudability of the paste, the material was treated using an EXAKT model 80E three-roll-mill and deaired subsequently. The resulting paste was then used to 3D-print a dental crown by means of an extrusion-based 3D-printing process (FIG. 1a). The pressure required to extrude the material at 65° C. was 2.4 bar. Viscosity of the material at 23° C. was 95±3 Pas.

Comparative Example 3

8.4 g of photocurable methacrylate-based monomer mixture as it is known in the art was compounded with 21.60 g of the same dental glass mixture as used in example 3. To improve extrudability of the paste, the material was treated using an EXAKT model 80E three-roll-mill and deaired subsequently. The resulting paste was then used to 3D-print a dental crown by means of an extrusion-based 3D-printing process (FIG. 1b). The pressure required to extrude the material at 65° C. was 3.0 bar. Viscosity of the material at 23° C. was 192±2 Pas.

FIGS. 1a and 1b clearly demonstrate the ability of the dental composition claimed for being used in the dental 3D-printing processes for manufacturing dental objects, such as dental crowns. The application of 20% of HUDMA (B) has been sufficient for reducing the finally achieved viscosity of the dental composition to the half. The other components of the respective composition have been kept. The pressure required has been successfully reduced by 20% hereby. The final outcome (the quality of the dental crown) has not changed as depictable in FIGS. 1a and 1b.

While the principles of the invention have been explained in relation to certain particular embodiments, and are provided for purposes of illustration, it is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the appended claims.

The invention claimed is:

1. Process for preparing a polymerizable compound having at least one optionally derivatized β-hydroxy urethane unit, which are represented by the following formula IIId-IIIg:

Formula IIId

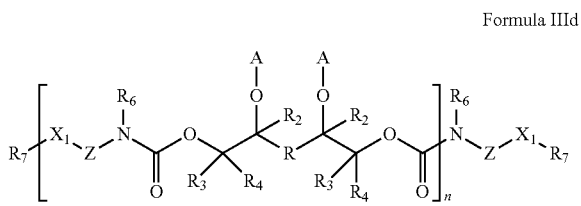

Formula IIIe

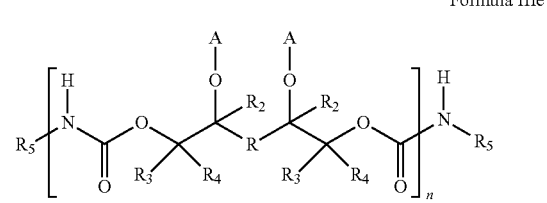

Formula IIIf

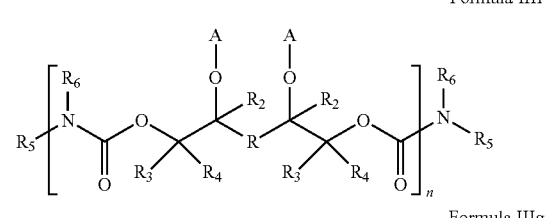

Formula IIIg

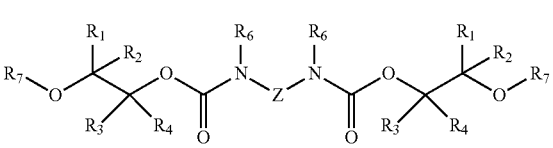

wherein
R represents a divalent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or unsubstituted or substituted $C_3$-$C_{18}$ heteroarylene group;

$R_1$ is an unsubstituted or substituted $C_{2-10}$ alkyl group, an unsubstituted or substituted $C_3$-$C_6$ cycloalkyl group, an unsubstituted or substituted $C_1$-$C_8$ cycloalkylalkylene, an unsubstituted or substituted $C_5$-$C_{18}$ aryl group, an unsubstituted or substituted $C_7$-$C_{24}$ aralkyl group, wherein each substituted group is substituted by one or more of a $C_{1-4}$ alkyl group, a $C_{1-4}$ alkoxy group, a hydroxyl group, an aryl group or an aryloxy group;

$R_2$, $R_3$ and $R_4$ are independent from each other, and represent a hydrogen or a $C_{1-4}$ alkyl group;

Z is a divalent aliphatic $C_{2-10}$ group, a divalent cycloaliphatic $C_3$-$C_6$ group or an aralkylene group having 7 to 24 carbon atoms, wherein each group optionally contain oxygen atoms and which is optionally substituted by $C_{1-4}$ alkyl group;

$R_5$ is a mono-valent aliphatic $C_{1-10}$ group, cycloaliphatic $C_3$-$C_6$ group or an aralkylene group having 7 to 24 carbon atoms;

$R_6$ is a hydrogen atom, a $C_{1-6}$ alkyl group, a $C_{3-10}$ cycloalkyl group, a $C_7$-$C_{12}$ aralkyl group, or an (meth)acryl group; wherein each group is optionally substituted by one or more of a $C_{1-4}$ alkyl group, a $C_{1-4}$ alkoxy group, or a hydroxyl group;

$R_7$ is $$\begin{array}{c} R_8 \\ \diagup \\ R_9 \end{array} \!\!= \!\! \begin{array}{c} \\ \diagdown \\ O \end{array} \!\!\!\!\!\!\!\begin{array}{c} \xi \\ \xi \end{array} ;$$

wherein $R_8$ is a hydrogen atom, or a linear $C_{1-3}$ or branched $C_{3-5}$ alkyl group substituted with a COOH group;

$R_9$ is a hydrogen atom, —COOH group, or a linear $C_{1-3}$ or branched $C_{3-5}$ alkyl group substituted with a COOH group;

A is independently same or different and is a hydrogen atom or $R_7$;

$X_1$ is an oxygen atom or a nitrogen atom substituted by $R_6$;

n is an integer of from 1 to 5;

said process comprising the steps of:
(a) reacting at least one component A having at least one cyclic carbonate group with at least one component B having at least one of primary amine functional group and secondary amine functional group to form an intermediate compound having at least one β-hydroxy urethane unit and residual —NH or —OH group; and
(b) reacting the intermediate compound having at least one β-hydroxy urethane unit and residual —NH or —OH group with at least one unsaturated mono- or poly-carboxylic acid to form a polymerizable compound having at least one derivatized β-hydroxy urethane unit, wherein
the at least one component A having at least one cyclic carbonate group is a compound of Formula I:

$$\left[ \begin{array}{c} R_3 \quad R_4 \\ \diagup \quad \diagdown \\ O \quad R_2 \\ | \quad | \\ O \quad Y \end{array} \!\!\!\! W\!\!-\!\!Q \right]_{\!\!m}\!\!\!\!-\!\!R_1 \qquad \text{Formula I}$$

wherein
$R_1$ represents a hydrogen, an m-valent $C_{1-22}$ hydrocarbon group, which group optionally includes 1 to 12 oxygen or sulfur atoms, and which is optionally substituted by $C_{1-4}$ alkyl group or a (meth)acrylate group;

$R_2$, $R_3$ and $R_4$ are independent from each other, and represent a hydrogen or a $C_{1-4}$ alkyl group;

W is an oxygen atom, —O—C=O— or a direct bond;

Q is a direct bond or a straight or branched chain alkylene having 1 to 4 carbons;

Y is a direct bond, an unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or an unsubstituted or substituted $C_3$-$C_{18}$ heteroarylene group; wherein each unsubstituted or substituted group optionally includes at least one of 1-6 oxygen atoms, nitrogen atoms or sulphur atoms; wherein each substituted groups is substituted by $C_{1-4}$ alkyl group;

m is an integer of from 1 to 6; and wherein the at least one component B having at least one of primary amine functional group and secondary amine functional group is a compound of Formula II:

$$\left[ \begin{array}{c} R_6 \\ | \\ H\!-\!N\!\!-\!\!(L_1X_2)_{\!p}\!\!-\!\!(L_2)_{\!q} \end{array} \right]_{\!r}\!\!\!\!-\!\!R_5\!\!-\!\!(L_2)_{\!q}\!\!-\!\!X_1\!\!-\!\!H \qquad \text{Formula II}$$

wherein
$R_5$ is a (r+1)-valent aliphatic $C_{2-10}$ group, cycloaliphatic $C_3$-$C_6$ group or an aralkylene group having 7 to 24 carbon atoms, wherein each group optionally contains oxygen or sulfur atoms and which is optionally substituted by $C_{1-4}$ alkyl groups;

$R_6$ is a hydrogen atom, a $C_{1-6}$ alkyl group, a $C_{3-10}$ cycloalkyl group, a $C_7$-$C_{12}$ aralkyl group, or an (meth)acryl group; wherein each group is optionally substituted by one or more of a $C_{1-4}$ alkyl group, a $C_{1-4}$ alkoxy group, or a hydroxyl group;

$L_1$ and $L_2$ are independently a same or different straight or branched chain alkylene having from 1 to 4 carbons;

$X_1$ is a direct bond, an oxygen atom or a nitrogen atom substituted by $R_6$;

$X_2$ is an oxygen atom;

p and q are integer of from 0 to 4; and r is an integer of from 1 to 6.

2. Process according to claim 1, characterized in that the at least one unsaturated mono- or poly-carboxylic acid is selected from the group consisting of acrylic acid, (meth)acrylic acid, itaconic acid, maleic acid and fumaric acid.

3. Process according to claim 1, characterized in that the intermediate compound having at least one β-hydroxy urethane unit and the residual —NH or —OH group is one of the following:

$$H\!\!-\!\!\left[ X_1\!\!-\!\!Z\!\!-\!\!\underset{\underset{O}{\|}}{N}\!\!-\!\!\underset{R_6}{\overset{H}{\underset{|}{N}}}\!\!-\!\!\underset{\underset{R_3'\ R_4'}{}}{\overset{\overset{H}{\underset{|}{O}}}{\underset{|}{}}}\!\!-\!\!R\!\!-\!\!\underset{\underset{R_3'\ R_4'}{}}{\overset{\overset{H}{\underset{|}{O}}}{\underset{|}{}}}\!\!-\!\!\underset{\underset{O}{\|}}{N}\!\!-\!\!\underset{R_6}{\overset{}{\underset{|}{N}}}\!\!-\!\!Z\!\!-\!\!X_1 \right]_{\!n}\!\!\!\!-\!\!H;$$

-continued

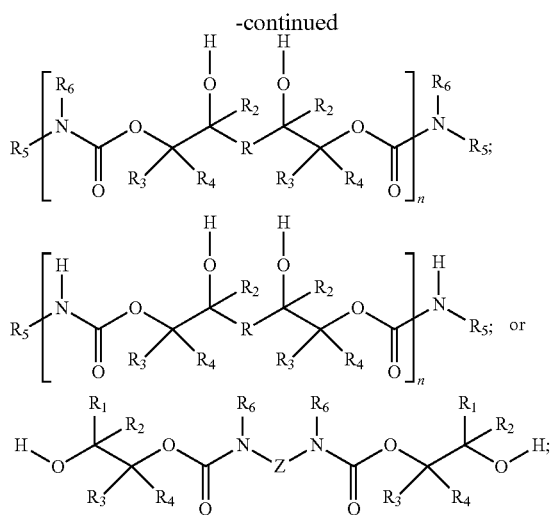

wherein

R represents a divalent unsubstituted or substituted $C_1$-$C_{18}$ alkylene group, an unsubstituted or substituted $C_3$-$C_8$ cycloalkylene group, an unsubstituted or substituted aralkylene group, an unsubstituted or substituted $C_5$-$C_{18}$ arylene group or unsubstituted or substituted $C_3$-$C_{18}$ heteroarylene group;

$R_1$ is an unsubstituted or substituted $C_{2-10}$ alkyl group, an unsubstituted or substituted $C_3$-$C_6$ cycloalkyl group, an unsubstituted or substituted $C_1$-$C_8$ cycloalkylalkylene, an unsubstituted or substituted $C_5$-$C_{18}$ aryl group, an unsubstituted or substituted $C_7$-$C_{24}$ aralkyl group, wherein each substituted group is substituted by one or more of a $C_{1-4}$ alkyl group, a $C_{1-4}$ alkoxy group, a hydroxyl group, an aryl group or an aryloxy group;

$R_2$, $R_3$ and $R_4$ are independent from each other, and represent a hydrogen or a $C_{1-4}$ alkyl group;

Z is a divalent aliphatic $C_{2-10}$ group, a divalent cycloaliphatic $C_3$-$C_6$ group or an aralkylene group having 7 to 24 carbon atoms, wherein each group optionally contain oxygen atoms and which is optionally substituted by $C_{1-4}$ alkyl group;

$R_5$ is a mono-valent aliphatic $C_{1-10}$ group, cycloaliphatic $C_3$-$C_6$ group or an aralkylene group having 7 to 24 carbon atoms;

$R_6$ is a hydrogen atom, a $C_{1-6}$ alkyl group, a $C_{3-10}$ cycloalkyl group, a $C_7$-$C_{12}$ aralkyl group, or an (meth) acryl group; wherein each group is optionally substituted by one or more of a $C_{1-4}$ alkyl group, a $C_{1-4}$ alkoxy group, or a hydroxyl group;

$X_1$ is an oxygen atom or a nitrogen atom substituted by $R_6$; and n is an integer of from 1 to 5.

* * * * *